United States Patent
Pak et al.

(10) Patent No.: US 7,759,284 B2
(45) Date of Patent: Jul. 20, 2010

(54) CALCINATION IN AN INERT GAS IN THE PRESENCE OF A SMALL CONCENTRATION OF AN OXIDIZING COMPONENT

(75) Inventors: Serguei Pak, Teaneck, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 1233 days.

(21) Appl. No.: 11/124,646

(22) Filed: May 9, 2005

(65) Prior Publication Data

US 2006/0252639 A1  Nov. 9, 2006

(51) Int. Cl.
- B01J 23/00 (2006.01)
- B01J 21/00 (2006.01)
- B01J 20/00 (2006.01)

(52) U.S. Cl. ............ 502/347; 502/317; 502/322; 502/323; 502/330; 502/348; 502/355; 502/415; 502/439

(58) Field of Classification Search ......... 502/243, 502/317, 322, 323, 347, 348, 355, 415, 439
See application file for complete search history.

(56) References Cited

U.S. PATENT DOCUMENTS

| | | | |
|---|---|---|---|
| 4,766,105 A * | 8/1988 | Lauritzen | 502/216 |
| 4,774,222 A * | 9/1988 | Rashkin | 502/347 |
| 4,820,675 A * | 4/1989 | Lauritzen | 502/216 |
| 4,829,044 A * | 5/1989 | Boxhoorn et al. | 502/348 |
| 5,077,256 A | 12/1991 | Yamamoto et al. | |
| 5,100,859 A * | 3/1992 | Gerdes et al. | 502/439 |
| 5,102,848 A * | 4/1992 | Soo et al. | 502/218 |
| 5,145,824 A * | 9/1992 | Buffum et al. | 502/216 |
| 5,364,826 A * | 11/1994 | Kemp | 502/315 |
| 5,374,748 A * | 12/1994 | Rizkalla | 549/534 |
| 5,447,897 A * | 9/1995 | Kemp | 502/303 |
| 5,504,052 A | 4/1996 | Rizkalla et al. | 502/347 |
| 5,504,053 A * | 4/1996 | Chou et al. | 502/348 |
| 5,525,740 A * | 6/1996 | Rizkalla | 549/534 |
| 5,545,603 A * | 8/1996 | Kemp | 502/347 |
| 5,597,773 A * | 1/1997 | Evans et al. | 502/348 |
| 5,602,070 A * | 2/1997 | Rizkalla | 502/347 |
| 5,625,084 A * | 4/1997 | Pitchai et al. | 549/536 |
| 5,646,087 A | 7/1997 | Rizkalla et al. | |

(Continued)

FOREIGN PATENT DOCUMENTS

WO  WO 2004/002954  1/2004

*Primary Examiner*—Cam N Nguyen
(74) *Attorney, Agent, or Firm*—Scully, Scott, Murphy & Presser, P.C.

(57) ABSTRACT

This invention relates to an improved process for preparing silver catalysts useful for the vapor phase production of ethylene oxide from ethylene and oxygen. An inert support is impregnated with a solution of a catalytically effective amount of a silver containing compound, a promoting amount of an alkali metal containing compound, and a promoting amount of a transition metal containing compound. The impregnated support is calcined by heating at a temperature of from about 200° C. to about 600° C. to convert the silver in the silver containing compound to metallic silver and to decompose and remove substantially all organic materials. The heating is conducted under an atmosphere comprising a combination of an inert gas and from about 10 ppm to about 5% by volume of a gas of an oxygen containing oxidizing component.

27 Claims, 1 Drawing Sheet

U.S. PATENT DOCUMENTS

| | | | |
|---|---|---|---|
| 5,686,380 A * | 11/1997 | Pitchai et al. | 502/347 |
| 5,691,269 A * | 11/1997 | Rizkalla | 502/347 |
| 5,705,661 A * | 1/1998 | Iwakura et al. | 549/536 |
| 5,780,656 A * | 7/1998 | Rizkalla et al. | 549/534 |
| 5,801,259 A * | 9/1998 | Kowaleski | 549/536 |
| 5,929,259 A * | 7/1999 | Lockemeyer | 549/534 |
| 6,103,916 A * | 8/2000 | Takada et al. | 549/534 |
| 6,153,556 A * | 11/2000 | Shima et al. | 502/348 |
| 6,184,175 B1 * | 2/2001 | Rizkalla | 502/347 |
| 6,600,056 B1 | 7/2003 | Mikawa et al. | |
| 6,750,173 B2 * | 6/2004 | Rizkalla et al. | 502/348 |
| 6,815,395 B2 * | 11/2004 | Shima et al. | 502/348 |
| 7,049,451 B2 * | 5/2006 | Ehara et al. | 549/534 |
| 2006/0293180 A1 * | 12/2006 | Thorsteinson | 502/347 |
| 2007/0184973 A1 * | 8/2007 | Lockemeyer et al. | 502/200 |
| 2007/0207914 A1 * | 9/2007 | Lockemeyer | 502/11 |

* cited by examiner

CALCINATION IN AN INERT GAS IN THE PRESENCE OF A SMALL CONCENTRATION OF AN OXIDIZING COMPONENT

BACKGROUND OF THE INVENTION

1. Field of the Invention

This invention relates to improved silver catalysts useful for the production of alkylene oxide, their preparation, and their use in alkylene oxide processes. More particularly, the invention is concerned with preparing a supported, metal promoted silver catalyst capable of oxidizing an alkene, preferably ethylene, with an oxygen containing gas in the vapor phase to produce alkylene oxide, preferably ethylene oxide, at high efficiencies and selectivities.

2. Description of the Related Art

It is known in the art to produce supported silver catalysts for the conversion of ethylene and oxygen to ethylene oxide. Many modifications have been proposed to improve the activity and selectivity of these catalysts. These modifications have involved improvements to the supports employed, the methods of production, the physical form of the silver on the support and the inclusion of additives to the catalyst composition. Methods are known for the preparation of supported silver catalysts useful for the vapor phase oxidation of ethylene to ethylene oxide, which involve impregnating a support such as alumina with a silver salt/amine solution. U.S. Pat. No. 3,702,359 is illustrative of such procedures.

U.S. Pat. No. 2,125,333 discloses the use of alkali metals, including both sodium or potassium and their salts as additives for various silver ethylene oxide catalysts. U.S. Pat. No. 2,615,900, cites a large number of useful promoters. U.S. Pat. No. 2,773,844, discloses a multistep silver deposition process. U.S. Pat. No. 3,575,888 discloses the use of aluminum oxide supports having a pore volume between about 0.15 and 0.30 $m^2/gm$ and surface area below about 10 $m^2/gm$. The use of small amounts of the alkali metals, K, Rb and Cs, were noted as useful promoters in supported silver catalysts in U.S. Pat. Nos. 3,962,136 and 4,010,115. U.S. Pat. No. 4,005,049 teaches the preparation of a silver/transition metal catalyst useful in oxidation reactions. In U.S. Pat. No. 4,536,482, catalytically active metals such as Ag and Re are co-sputtered along with a co-sputtered support material on a particular support. The preparation of silver catalysts which also contain alkali metal promoters by analogous procedures is shown, for example, in U.S. Pat. No. 3,962,136. Similar procedures for the preparation of silver catalysts promoted by an alkali metal and rhenium and also with a co-promoter selected from sulfur, molybdenum, tungsten, chromium and mixtures are shown in U.S. Pat. No. 4,766,105. Catalyst preparation by these prior art procedures has involved impregnating a support with a silver/amine solution which may contain the various promoters, and thereafter heating the impregnated support in a forced air oven up to a temperature of about 275° C. in order to reduce the silver to metallic silver and to separate volatiles from the catalyst.

U.S. Pat. No. 4,916,243 show silver catalysts for ethylene oxidation to ethylene oxide prepared by impregnating an inert support with a silver/amine and silver lactate solutions. The impregnated carriers were than heat treated on steel belt transported through a 2"×2" square heating zone for 2.5 minutes, the heating zone being maintained at 500° C. by passing hot air upward through the belt, or at 400° C. for 4 minutes.

U.S. Pat. No. 5,444,034 relates to silver catalyst preparation wherein a support is impregnated with a hydrocarbon solution of a silver salt of an organic acid and activated in stages up to a temperature of 500° C. under an inert gas such as nitrogen.

In other descriptions of processes of ethylene oxide production addition of oxygen-containing gases to the feed increased the efficiency. For example in U.S. Pat. No. 5,112,795 5 ppm of nitric oxide was added to the gas feed of composition: 8 volume % oxygen, 30 volume % ethylene, about 5 ppmw ethyl chloride and the balance nitrogen.

In the other processes to increase efficiency, particularly selectivity, the catalyst were treated at certain temperature and certain gas mixture. For example in U.S 2004/0049061 and 2004/002954 the selectivity of a highly selective epoxidation catalyst can be improved by heat-treating the catalyst in the presence of oxygen at a temperature which is typically above the catalyst's normal initial operation temperature.

U.S. Pat. Nos. 5,504,052 and 5,646,087 show silver catalysts for ethylene oxidation to ethylene oxide prepared by impregnating an inert support with a silver/amine solution as well as with various promoters and calcining the impregnated support at 300° C.-500° C., while the catalyst is maintained under an inert atmosphere. Thus the prior art teaches catalyst preparation by calcining an impregnated support either in air, i.e. a large amount of oxygen, or under an inert atmosphere such as nitrogen. It has been now been surprisingly found that the calcination of an impregnated support in an inert atmosphere, such as nitrogen, with the addition of only a small amount of an oxidizing gas, such as molecular oxygen in the inert atmosphere, improves the effective life, activity and selectivity of an ethylene oxide catalyst.

SUMMARY OF THE INVENTION

The invention provides a process for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 5% by volume of a gas of an oxygen containing oxidizing component.

The invention also provides a process for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 1% by volume of a gas of an oxygen containing oxidizing component.

The invention further provides a process for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 500 ppm by volume of a gas of an oxygen containing oxidizing component.

The invention still further provides a process for the oxidation of ethylene to ethylene oxide which comprises the vapor phase oxidation of ethylene with molecular oxygen in the presence of the above catalyst in a fixed bed, tubular reactor.

DETAILED DESCRIPTION OF THE INVENTION

Figure 1:
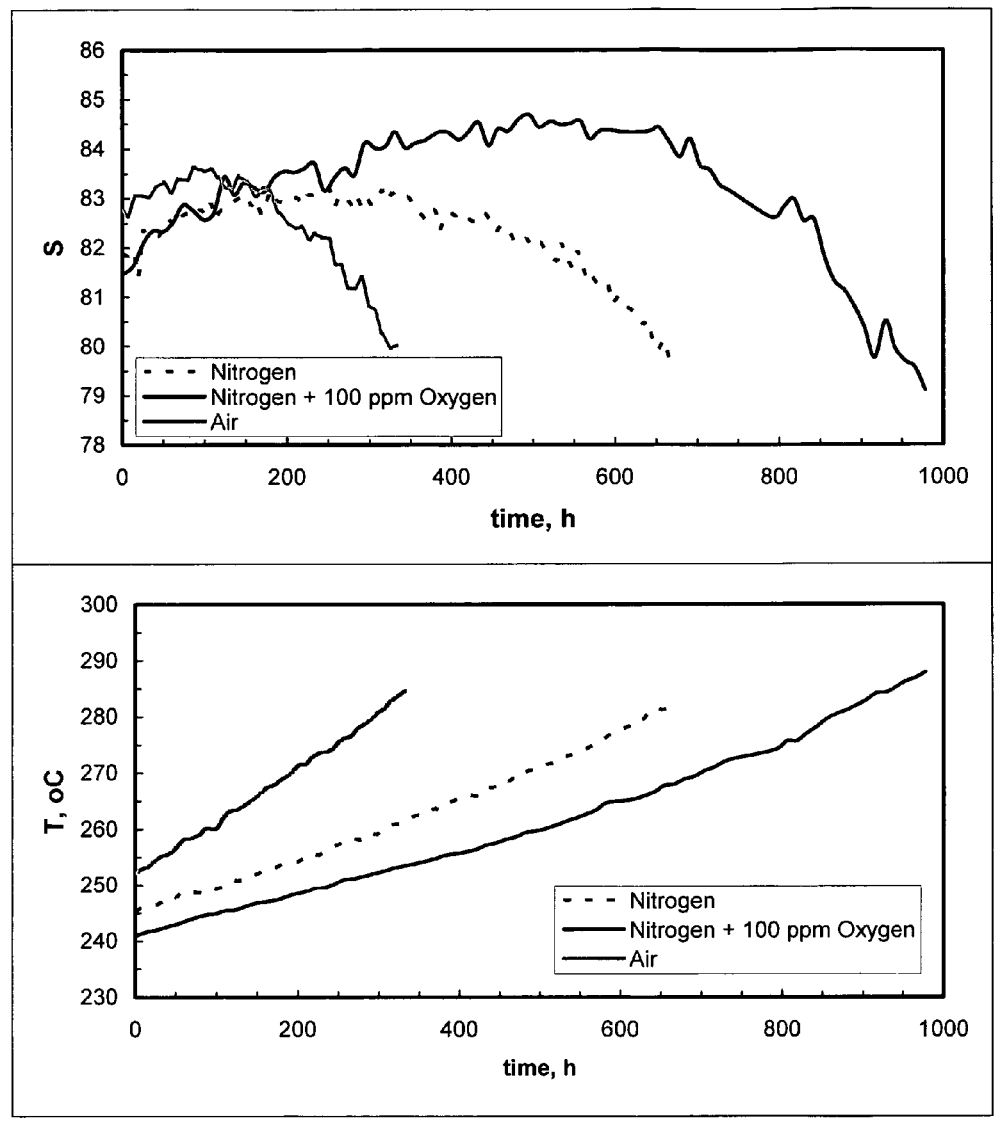
FIG. 1 is a graph of selectivity over time for catalyst calcined (A) in pure nitrogen, (B) in nitrogen with small oxygen addition, and (C) in air for the catalysts of the Example.

The catalysts of the invention are prepared by impregnating porous refractory supports with silver ions, compounds, complexes and/or salts dissolved in a suitable solvent sufficient to cause deposition of silver precursor compound onto the support. The impregnated carrier is then removed from the solution and the deposited silver compound is reduced to metallic silver by high temperature calcination. Also deposited on the support either prior to, coincidentally with, or subsequent to the deposition of the silver are suitable ions, compounds and/or salts of an alkali metal dissolved in a suitable solvent. Also deposited on the carrier either prior to, coincidentally with, or subsequent to the deposition of the silver and/or alkali metal are suitable transition metal ions, compounds, complexes and/or salts dissolved in an appropriate solvent.

The support or carrier employed useful for these catalysts may be a porous refractory catalyst carrier or support material which is relatively inert in the presence of the ethylene oxidation feed materials, products and reaction conditions. Such conventional materials are known to those skilled in the art and may be of natural or synthetic origin and preferably are of a macroporous structure, that is, a structure having a surface area of about 10 $m^2/g$ or less and preferably about 3 $m^2/g$ or less. Examples of supports that are useful as supports for the ethylene oxide catalysts of this invention are the aluminum oxides, especially alpha-alumina, charcoal, pumice, magnesia, zirconia, keiselguhr, fullers' earth, silicon carbide, porous agglomerates comprising silica and/or silicon carbide, silica, magnesia, selected clays, artificial and natural zeolites and ceramics. Preferred catalysts may be made with supports comprising alumina, silica, silica-alumina or combinations thereof. Most preferred supports are those principally containing alpha-alumina, particularly those containing up to about 15 wt % silica. In the case of alpha alumina containing supports, preferred are those having a surface area as measured by the B.E.T. method of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$, and a water pore volume as measured by conventional water absorption techniques of from about 0.1 cc/g to about 0.75 cc/g by volume preferably from about 0.25 cc/g to about 0.55 cc/g. The B.E.T. method for determining specific surface area is described in detail in Brunauer, S., Emmett, P. H. and Teller, E., J. Am. Chem. Soc., 60, 309-16 (1938). Pore volume and the pore size distribution are measured by a conventional mercury porosimeter method; see Drake and Ritter, "Ind. Eng. Chem. Anal. Ed.," 17, 787 (1945). Such carriers are commercially available from the Norton Company.

For use in commercial ethylene oxide production applications, the supports are desirably formed into regularly shaped pellets, spheres, rings, particles, chunks, pieces, pellets, wagon wheels, and the like of a size suitable for employment in fixed bed reactors. Desirably, the support particles may have "equivalent diameters" in the range of from about 3 mm to about 10 mm and preferably in the range of from about 4 mm to about 8 mm, which are usually compatible with the internal diameter of the tube reactors in which the catalyst is placed. "Equivalent diameter" is the diameter of a sphere having the same external surface (i.e. neglecting surface within the pores of the particle) to volume ratio as the support particles being employed.

A conventional porous refractory support as described above is impregnated with a silver impregnating solution, preferably an aqueous silver solution. The support is also impregnated at the same time or in a separate step with various catalyst promoters. Preferred catalysts prepared in accordance with this invention contain up to about 45% by weight of silver, expressed as metal, deposited upon the surface and throughout the pores of a porous refractory support. Silver contents, expressed as metal, of about 1-40% based on weight of total catalyst are preferred, while silver contents of 8-35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide and selectivity and activity stability within catalyst life. Useful silver containing compounds non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

This catalyst comprises a catalytically effective amount of silver, a promoting amount of alkali metal, a promoting amount of a transition metal supported on a porous, refractory support. As used herein the term "promoting amount" of a certain component of a catalyst refers to an amount of that component that works effectively to provide an improvement in one or more of the catalytic properties of that catalyst when compared to a catalyst not containing said component. The exact concentrations employed, of course, will depend upon, among other factors, the desired silver content, the nature of the support, the viscosity of the liquid, and solubility of the silver compound.

In addition to silver, the catalyst also contains an alkali metal promoter selected from lithium, sodium, potassium, rubidium, cesium or combinations thereof, with, cesium being preferred. The amount of alkali metal deposited on the support or catalyst or present on the support or catalyst is to be a promoting amount. Preferably the amount will range from about 10 ppm to about 3000 ppm, more preferably from about 15 ppm to about 2000 ppm and even more preferably from about 20 ppm to about 1500 ppm and yet even more preferably from about 50 ppm to about 1000 ppm by weight of the total catalyst, measured as the metal.

The catalyst also contains a transition metal promoter which comprises an element from Groups 5b, 6b, 7b and 8 of the Periodic Table of the Elements, and combinations thereof. Preferably the transition metal comprises an element selected from Group 7b of the Periodic Table of the Elements. More preferred transition metals are rhenium, molybdenum, and tungsten, with molybdenum and rhenium most preferred. The amount of transition metal promoter deposited on the support or catalyst or present on the support or catalyst is to be a promoting amount. The transition metal promoter may be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal.

The silver solution used to impregnate the support is may also comprise an optional solvent or complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount of from about 0.1 to about 5.0 moles of ethylene diamine per mole of silver, preferably from about 0.2 to about 4.0 moles, and more preferably from about 0.3 to about 3.0 moles of ethylene diamine for each mole of silver.

When a solvent it is used it may be water-based, or organic-based, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic-based solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of organic solvents, or of water and one or more organic solvents may be used, provided that such mixed solvents function as desired herein The concentration of silver salt in the solution is in the range of from about 0.1% by weight to the maximum permitted by the solubility of the particular salt/solubilizing agent combination employed. It is generally very suitable to employ silver salts solutions containing from 0.5% to about 45% by weight of silver with silver concentrations of from 5 to 30% by weight being preferred.

Impregnation of the selected support is achieved in conventional manners by excess solution impregnation, incipient wetness, etc. Typically support material is placed in the silver solution until a sufficient amount of the solution is absorbed by the support. Preferably the quantity of the silver solution used to impregnate the porous support is no more than is necessary to fill the pore volume of the porous support. The silver containing liquid penetrates by absorption, capillary action and/or vacuum into the pores of the support. A single impregnation or a series of impregnations, with or without intermediate drying, may be used, depending in part on the concentration of the silver salt in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888, which are incorporated herein by reference. Known prior procedures of pre-deposition, co-deposition and post-deposition of various the promoters can be employed.

Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to optimize conditions and results by taking into account feedstock costs, energy costs, by-product removal costs and the like. The particular combination of silver, support, alkali metal promoter, and transition metal promoter of the instant invention will provide an improvement in one or more catalytic properties over the same combination of silver and support and none, or only one promoter.

After impregnation, the support impregnated with silver precursor compound and the promoters is calcined or activated, for a time sufficient to reduce the silver component to metallic silver and to remove volatile decomposition products from the silver containing support. The calcination is accomplished by heating the impregnated support, preferably at a gradual rate, to a temperature in the range of from about 200° C. to about 600° C., preferably from about 250° C. to about 500° C., and more preferably from about 300° C. to about 450° C., at a reaction pressures in the range of from 0.5 to 35 bar, for a time sufficient to convert the contained silver to silver metal and to decompose all or substantially all of present organic materials and remove the same as volatiles. Useful heating times range from about 1 minute to about 12 hours, preferably from about 2 minutes to about 6 hours, and more from about 2 minutes to about 1 hour minutes. In general, the higher the temperature, the shorter the required reduction period. A wide range of heating periods have been suggested in the art to thermally treat the impregnated support, (e.g., U.S. Pat. No. 3,563,914 suggests heating for less than 300 seconds, U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range) it is only important that the reduction time be correlated with temperature such that substantially complete reduction of silver salt to catalytically active metal is accomplished. A continuous or step-wise heating program may be used for this purpose.

In accordance with this invention during heating, the impregnated support is maintained under an atmosphere comprising a combination of an inert gas and from about 10 ppm to about 5% by volume of a gas of an oxygen containing oxidizing component. For purposes of this invention, inert gases are defined as those which do not substantially react with the catalyst producing components under the catalyst preparation conditions chosen. These include nitrogen, argon, krypton, helium, and combinations thereof, with the preferred inert gas being nitrogen. The gas of an oxygen containing oxidizing component may include molecular oxygen, $CO_2$, NO, $NO_2$, $N_2O_3$, $N_2O_4$, or $N_2O_5$, or a substance capable of forming NO, $NO_2$, $N_2O_3$, $N_2O_4$, or $N_2O_5$ under calcining conditions, or combinations thereof, and optionally comprising $SO_3$, $SO_2$, $P2O_5$, $P_2O_3$ or combinations thereof. Of these molecular oxygen is preferred and more preferred is a combination of $O_2$ with NO or $NO_2$. In a useful embodiment, the atmosphere comprises from about 10 ppm to about 1% by volume of a gas of an oxygen containing oxidizing component. In another useful embodiment, the atmosphere comprises from about 50 ppm to about 500 ppm of a gas of an oxygen containing oxidizing component.

Ethylene Oxide Production

Generally, the commercially practiced ethylene oxide production processes are carried out by continuously contacting an oxygen containing gas with ethylene in the presence of the present catalysts at a temperature in the range of from about 180° C. to about 330° C. and preferably about 200° C. to about 325° C., more preferably from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1-5 seconds. Oxygen may be supplied to the reaction in an oxygen containing stream, such as air or as oxygen from a commercially available delivery source such as a tank. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.5 to 6 volume percent. A usual process for the oxidation of ethylene to ethylene oxide comprises the vapor phase oxidation of ethylene with molecular oxygen in the presence of a catalyst in a fixed bed, tubular reactor. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, a concentrated oxygen stream comprising oxygen in major amount with lesser amounts of one or more diluents such as nitrogen, argon, etc., or another oxygen containing stream such as air. The use of the present catalysts in ethylene oxidation reactions is in no way limited to the use of specific conditions among those which are known to be effective.

The resulting ethylene oxide is separated and recovered from the reaction products by conventional methods known and used in the art. Use of the silver catalysts of the invention in ethylene oxide production processes gives higher overall ethylene oxidation selectivities to ethylene oxide at a given ethylene conversion than are possible with conventional catalysts.

In the production of ethylene oxide, reactant feed mixtures may contain 0.5 to 45% ethylene and 3 to 15% oxygen, with the balance comprising comparatively inert materials including such substances as nitrogen, carbon dioxide, methane, ethane, argon and the like. In a preferred application of the silver catalysts of the invention ethylene oxide is produced when an oxygen containing gas of about 95% or more of oxygen. Only a portion of the ethylene usually is reacted per pass over the catalyst and after separation of the desired ethylene oxide product and the removal of appropriate purge stream and carbon dioxide to prevent uncontrolled build up of inerts and/or by-products, unreacted materials are returned to the oxidation reactor. For purposes of illustration only, the following are conditions that are often used in current commercial ethylene oxide reactor units.

| | |
|---|---|
| GHSV | 1500-10,000 |
| Inlet pressure | 150-400 psig |
| Inlet Feed: | |
| ethylene | 1-40% |
| $O_2$ | 3-12% |
| $CO_2$ | 2-40% |
| ethane | 0-3% |

Argon and/or methane and/or nitrogen:
0.3-20 ppmv total diluent chlorohydrocarbon moderator

| | |
|---|---|
| Coolant temperature | 180-315° C. |
| Catalyst temperature | 180° C. |
| $O_2$ conversion level | 10-60% |

EO Production (Work Rate) 2-16 lbs. EO/cu.ft. catalyst/hr.

The following non-limiting example serves to illustrate the invention.

Example

Carrier Preparation

A catalyst carrier was obtained by taking 1000 g of an alumina carrier as supplied by carrier manufacturer and, first, treating it with a circulating solution of 1300 g of 1.25 M NaOH in water. At the contact of NaOH solution with the carrier, the temperature was raised from room temperature to 80° C. in 30 minutes and then kept at this temperature for 1 hour. After treatment, the solution was drained and 1300 g of circulating deionized water at room temperature was used for rinsing the carrier for 1 hour after which it was drained. The rinsing procedure was repeated four more times. The treated carrier was dried at 150° C. overnight.

Catalyst A

Catalyst A was prepared by vacuum impregnation of the carrier with a silver-amine solution to a target 11.5% silver in the final product. Silver amine solution, also, contained a cesium promoter from CsOH was applied to target concentrations in final catalysts varying from 410 ppm to 650 ppm. The solution also contained rhenium from ammonium perrhenate solution to a targeted 280 ppm rhenium in the final catalysts. The impregnated carrier was calcined on a belt moving through a furnace in an environment of pure nitrogen with a maximum temperature of 400° C.

Catalyst B

Catalyst B was prepared by reproducing the preparation of Catalyst A except that the impregnated carrier was calcined on a belt moving through a furnace in the environment of nitrogen and 100 ppm oxygen.

Catalyst C

Catalyst C was prepared by reproducing the preparation of Catalyst A except that the impregnated carrier was calcined on a belt moving through a furnace in the environment of air.

Tests

Catalysts were compared in a test at weight Work Rate of 737 and the selectivity performance of the catalysts prepared on these carriers is presented on FIG. 1. FIG. 1 shows the selectivity over time for a catalyst calcined (A) in pure nitrogen, (B) in nitrogen with small oxygen addition, and (C) in air. The data clearly show the improved performance of the catalyst calcined in nitrogen with a small oxygen addition.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 5% by volume of a gas of an oxygen containing oxidizing component.

2. The process of claim 1 wherein the inert support comprises alpha alumina.

3. The process of claim 1 wherein the solution comprises an aqueous solution.

4. The process of claim 1 wherein the silver containing compound comprises silver oxalate, silver nitrate, silver oxide, silver carbonate, a silver carboxylate, silver citrate, silver phthalate, silver lactate, silver propionate, silver butyrate, silver fatty acid salts, and combinations thereof.

5. The process of claim 1 wherein the solution further comprises a component selected from the groups consisting of amines, alcohols, ammonia, lactic acid and combinations thereof.

6. The process of claim 1 wherein solution further comprises an amine.

7. The process of claim 1 wherein the solution further comprises an alkylene diamine having from 1 to 5 carbon atoms.

8. The process of claim 1 wherein the solution comprises silver oxalate and ethylene diamine.

9. The process of claim 1 wherein the gas of the oxygen containing oxidizing component comprises $CO_2$, NO, $NO_2$, $N_2O_3$, $N_2O_4$, or $N_2O_5$, or a substance capable of forming NO, $NO_2$, $N_2O_3$, $N_2O_4$, or $N_2O_5$ under calcining conditions, or combinations thereof, and optionally comprising $SO_3$, $SO_2$, $P_2O_5$, $P_2O_3$ or combinations thereof.

10. The process of claim 1 wherein the gas of the oxygen containing oxidizing component comprises $O_2$.

11. The process of claim 1 wherein the gas of the oxygen containing oxidizing component comprises $O_2$ in combination with NO or $NO_2$.

12. The process of claim 1 wherein the alkali metal containing compound comprises lithium, sodium, potassium, rubidium, cesium or combinations thereof.

13. The process of claim 1 wherein the alkali metal containing compound comprises cesium.

14. The process of claim 1 wherein the transition metal containing compound comprises an element selected from Groups 5b, 6b, 7b and 8 of the Periodic Table of the Elements, and combinations thereof.

15. The process of claim 1 wherein the transition metal containing compound comprises an element selected from Group 7b of the Periodic Table of the Elements, and combinations thereof.

16. The process of claim 1 wherein the transition metal containing compound comprises rhenium, molybdenum, tungsten or combinations thereof.

17. The process of claim 1 wherein the transition metal containing compound comprises molybdenum.

18. The process of claim 1 wherein the transition metal containing compound comprises rhenium.

19. The process of claim 1 wherein the inert gas comprises nitrogen, argon, krypton, helium, or combinations thereof.

20. The process of claim 1 wherein the inert gas comprises nitrogen.

21. The process of claim 1 wherein the atmosphere comprises from about 10 ppm to about 1% by volume of a gas of an oxygen containing oxidizing component.

22. The process of claim 1 wherein the atmosphere comprises from about 50 ppm to about 500 ppm of a gas of an oxygen containing oxidizing component.

23. The process of claim 1 wherein the heating is conducted for from about 1 minute to about 1 hour.

24. The process of claim 1 wherein the inert support comprises alpha alumina; the silver containing compound comprises silver oxalate, silver oxide, silver carbonate, silver lactate and combinations thereof; the alkali metal containing compound comprises lithium, sodium, potassium, rubidium, cesium or combinations thereof; wherein the transition metal containing compound comprises rhenium; wherein the inert gas comprises nitrogen, argon, krypton, helium, carbon dioxide, or combinations thereof; wherein the atmosphere comprises from about 10 ppm to about 1% by volume of a gas of the oxygen containing oxidizing component.

25. The process of claim 1 wherein the inert support comprises alpha alumina; the silver containing compound comprises silver oxalate, silver oxide, silver carbonate, silver lactate and combinations thereof; the alkali metal containing compound comprises cesium; wherein the transition metal containing compound comprises rhenium; wherein the inert gas comprises nitrogen; wherein the atmosphere comprises from about 10 ppm to about 500 ppm of the gas of an oxygen containing oxidizing component.

26. A process for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 1% by volume of a gas of an oxygen containing oxidizing component.

27. A process for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 500 ppm by volume of a gas of an oxygen containing oxidizing component.

* * * * *